United States Patent [19]

Beyerle et al.

[11] Patent Number: 4,598,079

[45] Date of Patent: Jul. 1, 1986

[54] 2-(ARYL SUBSTITUED)PIPERAZINONES AND NOOTROPIC COMPOSITIONS BASED THEREON

[75] Inventors: Rudi Beyerle; Heinz Bender, both of Frankfurt am Main; Ursula Schindler, Mörfelden-Walldorf; Rolf-Eberhard Nitz, Frankfurt am Main; Piero A. Martorana, Bad Homburg, all of Fed. Rep. of Germany

[73] Assignee: Cassella Aktiengesellschaft, Frankfurt am Main, Fed. Rep. of Germany

[21] Appl. No.: 610,921

[22] Filed: May 15, 1984

Related U.S. Application Data

[63] Continuation of Ser. No. 408,031, Aug. 13, 1982, abandoned.

[30] Foreign Application Priority Data

Aug. 20, 1981 [DE] Fed. Rep. of Germany ....... 3132882

[51] Int. Cl.$^4$ ................. C07D 241/02; C07D 409/04; C07D 403/04; A61K 31/495
[52] U.S. Cl. .................... 514/252; 544/121; 544/357; 544/360; 544/365; 544/373; 544/379; 544/384; 514/227; 514/247; 514/254
[58] Field of Search ............... 544/121, 357, 360, 365, 544/373, 379, 384; 424/250, 248.4

[56] References Cited

U.S. PATENT DOCUMENTS 3,390,139 6/1968 Benneville ........................... 544/384
3,935,214 1/1976 Zellner ................................ 544/357

Primary Examiner—George F. Lesmes
Assistant Examiner—S. A. Gibson
Attorney, Agent, or Firm—Berman, Aisenberg & Platt

[57] ABSTRACT

Aryl-substituted piperazinones and their physiologically-acceptable acid-addition salts have a useful nootropic action. They are administered enterally or parenterally in conventional dosage forms.

14 Claims, No Drawings

2-(ARYL SUBSTITUED)PIPERAZINONES AND NOOTROPIC COMPOSITIONS BASED THEREON

This application is a continuation of Ser. No. 408,031, filed Aug. 13, 1982, now abandoned.

The present invention relates to new piperazinones of the general formula I

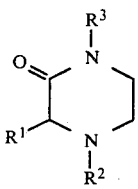

wherein $R^1$ denotes phenyl which is optionally substituted by alkoxy, fluorine, alkoxyalkyl or dialkylaminoalkoxy; 2-thienyl; 3-pyridyl; or a radical of the formula II

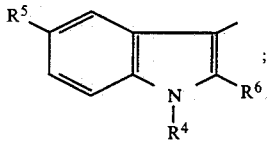

(wherein $R^4$ is hydrogen; alkyl; or phenalkyl which is optionally nuclearly substituted by chlorine; $R^5$ is hydrogen or alkoxy; and $R^6$ is hydrogen or phenyl); $R^2$ denotes hydrogen; alkyl which is optionally monosubstituted by alkoxycarbonyl or amidocarbonyl or N-substituted amidocarbonyl; lower alkenyl; lower alkynyl; phenalkyl which is optionally substituted by chlorine, hydroxyl or alkoxy; alkanoyl which is optionally substituted by chlorine; nicotinoyl; benzoyl which is optionally substituted by alkoxy, nitro or amino; amidosulphonyl or N-substituted amidosulphonyl; a radical of the formula III

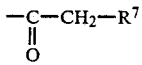

wherein $R^7$ is $-NH_2$, piperidin-1-yl, piperazin-1-yl, 4-alkylpiperazin-1-yl or

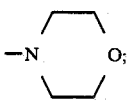

a radical of the formula

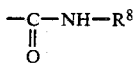

wherein $R^8$ is hydrogen, phenyl or phenyl substituted by chlorine; or a radical of the formula $-CH_2-CH_2-OR^9$ (V), wherein $R^9$ is hydrogen, phenoxyacetyl or a radical of the formula VI

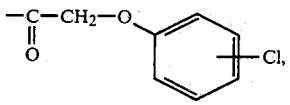

and $R^3$ denotes hydrogen; alkyl; alkoxycarbonylmethyl; amidocarbonylmethyl which is optionally N-monosubstituted or N-disubstituted or a group of the formula VII

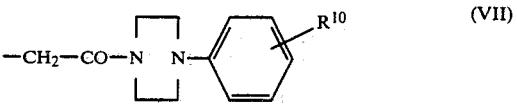

wherein $R^{10}$ is hydrogen or alkoxy; and to their physiologically acceptable acid-addition salts.

Throughout the disclosure and claims all references to alkyl (including the alkyl of each alkoxy, the alkyl of each phenalkyl, the alkyl of each alkylamino or dialkylamino, the alkyl of each alkoxycarbonyl, the alkyl of each alkanoyl and the alkyl of each alkylpiperazinyl) are directed to lower alkyl, i.e. alkyl with at most eight carbon atoms, unless otherwise specified. Each substituent of N-substituted amidocarbonyl or N-substituted amidosulphonyl ($R^2$) or of N-(mono- or di-)substituted amidocarbonylmethyl ($R^3$) is alkyl, phenyl, o-, m- or p-chlorophenyl or components which (with the amido nitrogen) comprise piperidinyl, piperazinyl or morpholino. Each reference in the examples to "ether" is to diethyl ether.

Suitable substituents for a phenyl radical represented by $R^1$ are, in addition to fluorine, especially alkoxy groups having 1–4 C atoms, alkoxyalkyl having a total of 2–6 C atoms or dialkylaminoalkoxy having a total of 3–6 C atoms.

Alkyl groups represented by $R^4$ and alkoxy groups represented by $R^5$ preferably have 1–4 C atoms. Phenalkyl represented by $R^4$ preferably has 1 or 2 C atoms in the alkyl radical.

A phenyl radical represented by $R^1$ has up to 3 substituents. If the phenyl radical is monosubstituted, the substituent is in the o-, m- or p-position in relation to the piperazinone ring. If the phenyl ring is disubstituted, the combinations 2,4-; 3,4-; 2,5- and 3,5- are preferred. If the phenyl ring is trisubstituted, the preferred points of substitution are 2,4,6- and 3,4,5-. A phenyl radical represented by $R^1$ advantageously has not more than one substituent of fairly large volume, such as, for example, a dialkylaminoalkoxy group. On the other hand, up to three of the smaller substituents, fluorine or, in particular, methoxy, are optionally attached to the phenyl radical.

A phenalkyl radical represented by $R^4$ is optionally substituted by chlorine, in particular by 1 or 2 chlorine atoms, which are, e.g., in the o-, m- or p-position, or in the 2,3-; 2,5-; 3,4- or 3,5-positions, respectively.

The following are examples of substituents which can be represented by $R^1$: phenyl, o-, m- or p-methoxyphenyl, o-, m- or p-ethoxyphenyl, 2,4-; 3,4- or 3,5-dimethoxyphenyl, 2,4,5-; 2,4,6- or 3,4,5-trimethoxyphenyl, o-, m- or p-fluorophenyl, 2,4-; 2,5-; 3,4- or 3,5-difluorophenyl, o-, m- or p-methoxymethylphenyl, o-, m- or p-ethoxymethylphenyl, o-, m- or p-propoxymethylphenyl, o-, m- or p-butoxymethylphenyl, o-, m- or p-methoxyethylphenyl, o-, m- or p-ethoxyethylphenyl, o-, m- or p-propoxyethylphenyl, o-, m- or p-butoxyethylphenyl, o-, m- or p-methoxypropylphenyl, o-, m- or p-ethoxypropylphenyl, o-, m- or p-propoxypropylphenyl, o-, m- p-butoxypropylphenyl, o-, m- or p-butoxybutylphenyl, 2,4-, 3,4-, 2,5- or 3,5-bis-methoxymethylphenyl, 2,4-, 3,4-, 2,5- or 3,5-bis-methoxyethylphenyl, 2,4-, 3,4-, 2,5- or 3,5-bis-ethoxymethylphenyl, o-, m- or p-dimethylaminoethoxyphenyl, o-, m- or p-diethylaminoethoxyphenyl, o-, m- or p-dipropylaminoethoxyphenyl, o-, m- or p-dimethylaminopropoxyphenyl, o-, m- or p-diethylaminopropoxyphenyl, o-, m- or p-diethylaminobutoxyphenyl, o-, m- or p-dimethylaminobutoxyphenyl, 2-thienyl, 3-pyridyl or the 1-indol-3-yl radical of the formula II in which $R^4$ denotes hydrogen, methyl, ethyl, benzyl, o-, m- or p-chlorobenzyl, phenethyl or o-, m- or p-chlorophenethyl, and in which $R^5$ denotes hydrogen, methoxy or ethoxy and in which $R^6$ denotes hydrogen or phenyl.

The following are examples of radicals represented by $R^1$ which are particularly preferred: phenyl, o-, m- or p-methoxyphenyl, 2,4-; 3,4- or 3,5-dimethoxyphenyl, 3,4,5-trimethoxyphenyl, o-, m- or p-fluorophenyl, o-, m- or p-methoxymethylphenyl, o-, m- or p-ethoxymethylphenyl, o-, m- or p-methoxyethylphenyl, o-, m- or p-ethoxyethylphenyl, o-, m- or p-dimethylaminoethoxyphenyl, o-, m- or p-diethylaminoethoxyphenyl, 2-thienyl, 3-pyridyl or the indol-3-yl radical of the formula II (in which $R^4$ denotes hydrogen, methyl, ethyl, benzyl, o-, m- or p-chlorobenzyl or phenethyl; in which $R^5$ denotes hydrogen, methoxy or ethoxy and in which $R^6$ denotes hydrogen or phenyl).

An alkyl radical or alkanoyl radical represented by $R^2$ preferably has 1–4 carbon atoms.

An alkyl radical, particularly a methyl radical, represented by $R^2$ is optionally substituted by alkoxycarbonyl having a total of 2 to 5 carbon atoms, or by amidocarbonyl, and the amino group of the amidocarbonyl radical is, in turn, optionally monosubstituted or disubstituted by methyl or ethyl, or is a member of a piperidine, piperazine or morpholine ring; an alkanoyl radical represented by $R^2$ is also optionally substituted, preferably monosubstituted, by chlorine. Phenalkyl represented by $R^2$ has 1 to 3 carbon atoms in the alkyl radical; the phenalkyl radical represented by $R^2$ is optionally nuclearly monosubstituted or disubstituted by chlorine or monosubstituted, disubstituted or trisubstituted by alkoxy having 1 or 2 carbon atoms or by an OH group. In the case of monosubstitution, the substituents are in the o-, m- or p-position in relation to the alkylene bridge; in the case of disubstitution, the positions 2,4-; 3,4-; 2,5-; and 3,5- are particularly advantageous; and, in the case of trisubstitution, the substituents are preferably in the 2,4,5-; 2,4,6- and 3,4,5-positions. An OH group is optionally present in the phenyl nucleus, preferably in the 2-position and particularly when the phenalkyl radical contains 3 C atoms in the alkyl chain. A benzoyl group represented by $R^2$ is optionally substituted (in the phenyl radical) by 1 to 3 alkoxy groups having 1 or 2 carbon atoms, or by 1 or 2 nitro or amido groups. The same indications apply to the positions of the substituents as apply to the substituted phenalkyl radicals represented by $R^2$. The amido group of an amidosulphonyl represented by $R^2$ is preferably N-substituted, specifically substituted by 1 or 2 alkyl group, each of which has 1–4, preferably 1–2, C atoms, or it is a member of a piperidine, piperazine, 4-alkylpiperazine or morpholine ring, in which connection alkylpiperazine has 1–4, preferably 1–2, C atoms in the alkyl radical.

A 4-alkylpiperazin-1-yl radical represented by $R^7$ has 1–4, preferably 1–2, C atoms in the alkyl group.

In a chlorine-substituted phenyl represented by $R^8$, 1 or 2 chlorine atoms are present, which are either, in the case of monosubstitution, in the o-, m- or p-position in relation to the NH group, or, in the case of disubstitution, in the 2,4-, 2,5-, 3,4- or 3,5-positions. In a chlorophenoxyacetyl radical of the formula VI represented by $R^9$ the chlorine atom is in the o-, m- or p-position in relation to the oxygen.

The following are examples of substituents represented by $R^2$: methyl, ethyl, propyl, isopropyl, butyl, isobutyl, tert.-butyl, methoxycarbonylmethyl, methoxycarbonylethyl, ethoxycarbonylmethyl, ethoxycarbonylethyl, propoxycarbonylmethyl, butoxycarbonylmethyl, amidocarbonylmethyl, amidocarbonylethyl, dimethylamidocarbonylmethyl, diethylamidocarbonylmethyl, piperidinylcarbonylmethyl, piperazinylcarbonylmethyl, morpholinylcarbonylmethyl, benzyl, o-, m- or p-chlorobenzyl, 2,4-, 3,4-, 2,5- or 3,5-dichlorobenzyl, o-, m- or p-methoxybenzyl, o-, m- or p-ethoxybenzyl, 2,4-, 2,5-, 3,4- or 3,5-dimethoxybenzyl, 2,4-, 2,5-, 3,4- or 3,5-diethoxybenzyl, 2,4,5-, 2,4,6- or 3,4,5-trimethoxybenzyl, phenethyl, o-, m- or p-chlorophenethyl, 2,4-, 2,5-, 3,4- or 3,5-dichlorophenethyl, o-, m- or p-methoxyphenethyl, o-, m- or p-ethoxyphenethyl, 2,3-, 2,5-, 3,4- or 3,5-dimethoxyphenethyl, 2,4-, 2,5-, 3,4- or 3,5-diethoxyphenethyl, 2,4,5-, 2,4,6- or 3,4,5-trimethoxyphenethyl, 3-phenylprop-1-yl, 3-(o-, m- or p-methoxyphenyl)-prop-1-yl, 3-(o- or m-ethoxyphenyl)-prop-1-yl, 2-hydroxy-3-phenylprop-1-yl, 2-hydroxy-3-(o-, m- or p-methoxyphenyl)-prop-1-yl, 2-hydroxy-3-(o-, m- or p-ethoxyphenyl)-prop-1-yl, formyl, acetyl, chloroacetyl, propionyl, or α-chloropropionyl, butyryl, nicotinoyl, benzoyl, o-, m- or p-methoxybenzoyl, o-, m- or p-ethoxybenzoyl, 2,4-, 2,5-, 3,4- or 3,5-dimethoxybenzoyl, 2,4-, 2,5-, and 3,4- or 3,5-diethoxybenzoyl, 2,4,5-, 2,4,6- or 3,4,5- trimethoxybenzoyl, o-, m- or p-nitrobenzoyl, 2,4-dinitrobenzoyl, o-, m- or p-aminobenzoyl, 2,4-diaminobenzoyl, dimethylaminosulphonyl, diethylaminosulphonyl, aminoacetyl, morpholinylacetyl, aminocarbonyl, phenylaminocarbonyl, o-, m- or p-chlorophenylaminocarbonyl, hydroxyethyl, phenoxyacetoxyethyl or o-, m- or p-chlorophenoxyacetoxyethyl. The following are examples of particularly preferred meanings for $R^2$: hydrogen, methyl, ethyl, amidocarbonylmethyl, dimethylamidocarbonylmethyl, methoxycarbonylmethyl, ethoxycarbonylmethyl, piperidinylcarbonylmethyl, morpholinylcarbonylmethyl, benzyl, o-, m- or p-chlorobenzyl, o-, m- or p-methoxybenzyl, o-, m- or p-ethoxybenzyl, 2,4-, 2,5-, 3,4- or 3,5-dimethoxybenzyl, phenethyl, o-, m- or p-methoxyphenethyl, o-, m- or p-ethoxyphenethyl, 2,3-, 2,5-, 3,4- or 3,5-dimethoxyphenethyl, 3-phenylprop-1-yl, 2-hydroxy-3-phenylprop-1-yl, 2-hydroxy-3-(o-, m- or p-methoxyphenyl)-prop-1-yl, 2-hydroxy-3-(o-, m- or p-ethoxyphenyl)-prop-1-yl, formyl, acetyl, chloroacetyl, propionyl, nicotinoyl, benzoyl, o-, m- or p-methoxybenzoyl, 2,4-, 2,5-, 3,4- or 3,5-dimethoxybenzoyl, 3,4,5-trimethoxybenzoyl, o-, m- or p-nitrobenzoyl, o-, m- or p-aminobenzoyl, dimethylaminosulphonyl, aminoacetyl, morpholinylacetyl, aminocarbonyl, phenylaminocarbonyl, o-, m- or p-chlorophenylaminocarbonyl, hydroxyethyl, phenoxyacetoxyethyl or o-, m- or p-chlorophenoxyacetoxyethyl.

Alkyl radicals represented by $R^3$ advantageously have 1–4 carbon atoms.

An alkoxycarbonylmethyl group represented by $R^3$ preferably has 3 to 6 carbon atoms. An amidocarbonylmethyl group represented by $R^3$ is optionally substituted on the amino group by alkyl radicals and has, e.g., a total of 3 to 5 carbon atoms.

An alkoxy group ($R^{10}$) which is attached to the phenyl radical of a group of the formula VII represented by $R^3$ advantageously has 1 to 4, preferably 1 to 2, C atoms and is in the o-, m- or p-position in relation to the nitrogen of the piperazine ring.

The following are examples of substituents represented by $R^3$: methyl, ethyl, propyl, isopropyl, but-1-yl, but-2-yl, isobutyl, tert.-butyl, methoxycarbonylmethyl, ethoxycarbonylmethyl, propoxycarbonylmethyl, butoxycarbonylmethyl, amidocarbonylmethyl, monomethylamidocarbonylmethyl, monoethylamidocarbonylmethyl, monopropylamidocarbonylmethyl, mononbutylamidocarbonylmethyl, dimethylaminocarbonylmethyl, diethylamidocarbonylmethyl, 4-phenylpiperazin-1-ylcarbonylmethyl, 4-(o-, m- or p-methoxyphenyl)-pyridazin-1-ylcarbonylmethyl or 4-(o-, m- or p-ethoxyphenyl)-pyridazin-1-ylcarbonylmethyl.

The following are preferred meanings for $R^3$: hydrogen, methyl, ethyl, methoxycarbonylmethyl, ethoxycarbonylmethyl, propoxycarbonylmethyl, butoxycarbonylmethyl, amidocarbonylmethyl, monomethylamidocarbonylmethyl, monoethylamidocarbonylmethyl, dimethylaminocarbonylmethyl, 4-phenylpiperazin-1-ylcarbonylmethyl or 4-(or-, m- or p-methoxyphenyl)-pyridazin-1-ylcarbonylmethyl.

Piperazinones, according to the invention, of the formula I which have several of the abovementioned preferred structural characteristics are particularly preferred.

The invention includes all acid-addition salts. Those which are not physiologically acceptable are readily converted by conventional procedures to either corresponding free bases or to physiologically-acceptable acid-addition salts. Even those acid-addition salts which are regarded as substantially insoluble in common solvents are sufficiently dispersible in available media to convert them to corresponding free bases by recognized and available procedures.

The preparation of piperazinones, according to the invention, of the general formula I

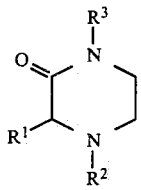
(I)

wherein $R^1$, $R^2$ and $R^3$ have the meanings indicated above, or of their physiologically acceptable acid addition salts, is effected by a procedure in which 5,6-dihydro-2(1H)-pyrazinones of the formula VIII

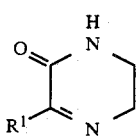
(VIII)

wherein $R^1$ denotes phenyl which is optionally substituted by alkoxy, fluorine, alkoxyalkyl or dialkylaminoalkoxy; 2-thienyl; 3-pyridyl; or a radical of the formula II

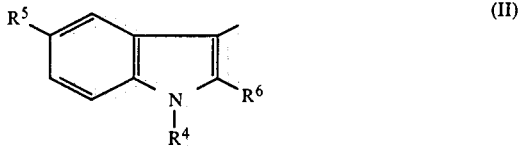
(II)

(wherein $R^4$ is hydrogen; alkyl; or phenalkyl which is optionally substituted by chlorine; $R^5$ is hydrogen or alkoxy, and $R^6$ is hydrogen or phenyl), are reduced to give the corresponding piperazinone of the formula I in which $R^2$ and $R^3$ are hydrogen, this piperazinone is, if appropriate, then reacted, in a manner which is in itself known, with an alkylating or acylating agent of the formula IX

$X—R^2$ (IX)

wherein X is a radical which can be removed as an anion, and $R^2$ denotes alkyl which is optionally substituted by alkoxycarbonyl or by amidocarbonyl; phenylalkyl which is optionally substituted by chlorine, or alkoxy; alkanoyl; nicotinoyl; benzoyl, which is optionally substituted by alkoxy, nitro or amino; amidosulphonyl or N-substituted aminosulphonyl; a radical of the formula III

(III)

wherein $R^7$ is $—NH_2$, piperidin-1-yl, piperazin-1-yl, 4-alkylpiperazin-1-yl or

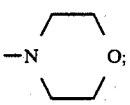

a radical of the formula

(IV)

wherein $R^8$ is hydrogen, phenyl or phenyl which is substituted by chlorine; or a radical of the formula $—CH_2—CH_2—OR^9$ (V), wherein $R^9$ is hydrogen, phenoxyacetyl or a radical of the formula VI

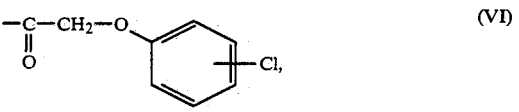
(VI)

and, if appropriate, the resulting piperazinone of the formula I (in which $R^3$ is hydrogen) is then reacted, in a manner which is in itself known, with an alkylating agent of the formula X

$X—R^3$ (X)

wherein X is a radical which can be removed as an anion, and $R^3$ denotes alkyl; alkoxycarbonylmethyl;

amidocarbonylmethyl which is optionally N-monosubstituted or N-disubstituted, or a group of the formula VII

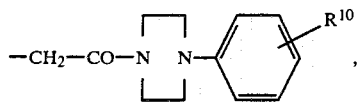

wherein $R^{10}$ is hydrogen or alkoxy, and the resulting product is, if desired, reacted in a manner which is in itself known with a physilogically-acceptable acid to give the acid addition salt.

Preferred piperazinones of the formula I are obtained if 5,6-dihydro-2(1H)-pyrazinones of the formula VIII, alkylating agents or acylating agents of the formula IX and alkylating agents of the formula X in which $R^1$, $R^2$ or $R^3$ have the particularly advantageous or preferred meanings mentioned above are employed.

A hydrogenation of the 3,4-double bond takes place when the 5,6-dihydro-2(1H)-pyrazinones of the formula VIII are reduced to give the corresponding piperazinones, according to the invention, of the formula I in which $R^2$ and $R^3$ are hydrogen. Analogous reductions are known in large numbers and suitable reducing agents and the reaction conditions are both provided by the literature. (Compare, for example, Methoden der Organ. Chemie ["Methods of Organic Chemistry"] (Houben-Weyl) 4th edition, Stuttgart 1957 volume 11/1, pages 692 et seq.).

Catalytically-activated hydrogen and complex hydrides, such as, for example, an alkali-metal borohydride or an alkali metal aluminium hydride, are particularly suitable for the preparation of the piperazinones according to the invention from the dihydropyrazinones of the formula VIII. The reduction is advantageously carried out in an inert organic solvent. If hydrogen is used as the reducing agent, the catalyst employed is, e.g., Raney nickel or Raney cobalt if the reaction is carried out at an elevated temperature, preferably between 50° and 100° C., or a noble metal catalyst, such as finely-divided platinum or palladium, advantageously on a suitable support, such as, for example, active charcoal, if the reaction is carried out at room temperature or at a slightly elevated temperature. Reduction using complex hydrides is frequently carried out at temperatures as low as room temperature, but the reaction is accelerated in a customary manner by warming, for example warming to the boiling point of a solvent which preferably boils below 100° C.

If catalytically activated hydrogen is employed, examples of suitable solvents are lower alcohols, such as methanol, ethanol or propanol; lower carboxylic acids, such as acetic acid; the esters of lower carboxylic acids with lower alcohols, such as ethyl acetate, and ethers, such as ethylene glycol monomethyl or dimethyl ether or tetrahydrofuran.

Reduction with an alkali-metal borohydride is carried out, for example, in lower alcohols, such as methanol or ethanol, while reduction with an alkali metal aluminium hydride is preferably carried out in anhydrous ethers, such as diethyl ether, dioxane or tetrahydrofuran.

The compounds of the formula I in which only $R^3$ is hydrogen, whereas $R^2$ has, within the scope of the definitions indicated above, a meaning other than hydrogen, are obtained by alkylation or acylation even under mild conditions from the piperazinones, according to the invention, of the formula I in which $R^2$ and $R^3$ are hydrogen and which are obtained by the reduction. The alkylating or acylating agents required for the alkylation or acylation, respectively, and the reaction conditions under which alkylation or acylation is carried out, are both known from the literature (compare Methoden der organ. Chemie ["Methods of Organic Chemistry"] (Houben-Weyl) 4th edition, Stuttgart 1957, volume 11/1, pages 24 et seq. and 11/2, pages 3 et seq.). In principle, alkylating or acylating agents of the formula IX indicated above are always employed. Examples of radicals X which are split off an anions are halogen atoms, in particular chlorine, bromine or iodine, or one equivalent of a sulphato group or, which is less usual, however, a quaternary ammonium group or a ternary sulphonium group. In the event that $R^2$ is alkyl or substituted alkyl, X preferably represents halogen, such as chlorine, bromine or iodine, and in the event that $R^2$ is an acyl radical, X usually denotes halogen, in particular chlorine or bromine, or a radical of the formula $R^2O$. The reaction is usually carried out in an inert organic solvent. It is advantageous to add a base to the mixture in order to capture the proton which has been split off. If piperazinones, according to the invention, of the formula I in which the 1-position is also substituted, that is to say $R^3$ is not hydrogen, are to be prepared, the compounds obtained in the first alkylation or acylation stage are subjected to a second alkylation stage. Alkylating agents of the formula $X-R^3$ in which X has, in principle, the same meanings as those already indicated above for the compounds of the formula $X-R^2$, are employed for this stage. This second alkylation is, as a rule, also effected in an organic solvent and the reaction is carried out in the presence of a base, e.g., in a basic medium. The reaction conditions for this stage are made more severe, compared with the conditions for the first alkylation, that is to say the reaction is carried out as a rule in a more strongly polar solvent and using a more active base, for example a base which is soluble in the reaction medium. Examples of solvents employed for the reaction with compounds of the formula $X-R^2$ are lower alcohols, e.g. alcohols having 1–4 C atoms, benzene derivatives, such as toluene or chlorobenzene, and ethers and cyclic ethers, such as, for example, tetrahydrofuran or dioxane. Polar solvents, such as, for example dimethylformamide, dimethyl sulphoxide or pyridine, are preferred as solvents for the reaction with a compound of the formula $X-R^3$.

Inorganic compounds which do not have to be soluble in the medium used, such as, for example, alkali metal salts of weak acids, for example alkali-metal acetates, carbonates, bicarbonates or phosphates and also magnesium oxide or calcium oxide, suffice as bases for the first alkylation or acylation stage using compounds of the formula $X-R^2$. The bases employed in the alkylation using compounds of the formula $X-R^3$ are preferably soluble in the reaction medium; it is advantageous to employ alkali metal hydroxides or alcoholates in this case.

Acid-addition salts of the compounds, according to the invention, of the formula I are prepared by dissolving the latter in an organic solvent and adding a solution of the desired acid in an organic solvent which is advantageously miscible with the solvent employed for I. Thus, for example, the hydrochlorides of the piperazinones, according to the invention, of the formula I are obtained by dissolving the compounds in alcohol and adding an equivalent quantity of a solution of hydrogen chloride in ether to the alcoholic solution.

The piperazinones, according to the invention, of the formula I and their physiologically acceptable salts are nootropic agents, that is to say they are used for treating diseases which are characterised by a limitation of the cerebral function, particularly the memory performance, and also for lessening cerebral aging processes. They are, surprisingly, considerably superior to the compounds hitherto known which have the same action. They exhibit an excellent activity in a variety of tests, such as, for example, in prolonging the survival time under sodium nitrite hypoxia by the method of Gibsen and Bless (J. Neurochemistry 27 [1976]) and in improving tolerance to hypoxia induced by nitrogen, in which experimental animals are subjected to respiration with pure nitrogen after premedication with the preparation under investigation and the prolongation of the interval between the start of the respiration and electrical neutrality of the electro-encephalogram, and also the lethality, are measured. The products according to the invention also have a very good action in tests which are directly aimed at measuring the learning and memory performance, such as, for example, the known "avoidance" tests.

Testing in the tests mentioned and in a number of further tests shows that, while the compounds according to the invention have a low toxicity, they have, surprisingly, a particularly advantageous profile of action which is not present in this form in known preparations.

The piperazinones according to the invention are administered to humans on their own, as mixtures with one another or in pharmaceutical preparations which contain, as the active constituent, an effective dose of at least one piperazinone according to the invention, or an acid-addition salt thereof, together with customary pharmaceutically-acceptable excipients and additives.

Examples of suitable excipients are water, vegetable oils, starch, gelatin, lactose, magnesium stearate, waxes, petroleum jelly etc. Examples of optional additives are wetting agents, disintegrants, preservatives, etc.

Suitable dosages vary within wide limits and are adapted in each particular case to individual factors. In general, a daily dose of from about 0.1 to 150 mg, preferably from 1 to 30 mg, per human individual of active substance is appropriate for oral administration. In the case of other administration forms too, owing to good absorption of the active compounds, the daily dose is within similar ranges, i.e. generally from 0.1 to 150 mg/person. The daily dose is normally administered in several partial, for example 2 to 4 doses, the single dosis containing 0.001 to 1 mg per kg of body weight of the active substance.

The pharmaceutical formulations generally contain from 0.1 to 50 mg/dose, preferably from 0.5 to 10 mg/dose, of active compound of formula I or a pharmacologically-acceptable acid-addition salt thereof.

The pharmaceutical preparations are in the form of, for example, tablets, capsules, aqueous or oily solutions or suspensions, emulsions, injectable aqueous or oily solutions or suspensions, dispersible powders or aerosol mixtures. Besides the compounds of the general formula I, the pharmaceutical preparations optionally also contain one or more other pharmaceutically-active substances, for example agents which stimulate the flow of blood, such as dihydroergocristine, nicergoline, buphenine, nicotinic acid and esters thereof, pyridyl carbinol, bencyclane, cinnarizine, naftidrofuryl, raubasine and vincamine; compounds having a positive inotropic action, such as digoxin, acetyldigoxin, metildigoxin and lanato-glycosides; coronary dilators, such as carbocromen, dipyridamole, nifedipine and perhexiline; anti-angina compounds, such as isosorbide dinitrate, isosorbide mononitrate, glycerol trinitrate, molsidomine and verapamil; β-blockers, such as propranolol, oxprenolol, atenolol, metoprolol and penbutolol, and oogenic-metabolic agents, such as pirilinol. In addition, the compounds can be combined with other substances having a nootropic action, such as, for example, piracetam. In addition, the compounds are optionally combined with other substances having a nootropic action, such as, for example, piracetam.

The illustrative embodiments which follow illustrate the preparation of the compounds according to the invention. The reaction conditions and the reducing, alkylating and acylating agents are alternatively varied within the scope of the state of the art and of the patent claims, and the 5,6-dihydro-2(1H)-pyrazinones employed are also varied within the scope of the patent claims.

EXAMPLE 1

3-(3,4-dimethoxyphenyl)-piperazin-2-one 23.4 g (0.1 mol) of 3-(3,4-dimethoxyphenyl)-5,6-dihydro-2(1H)-pyrazinone are dissolved in 230 ml of ethanol and hydrogenated, in the presence of Raney nickel as the catalyst, at 40° to 60° C. and under a hydrogen pressure of 50 bar until saturation is reached. The catalyst is then filtered off, the filtrate is evaporated in vacuo and the residue is triturated with ether.

Yield: 22.9 g=97.8% of theory (molecular weight 236),

Melting point: 124°–126° C.

EXAMPLE 2

3-(3,4-dimethoxyphenyl)-4-benzylpiperazin-2-one 47.2 g (0.2 mol) of the 3-(3,4-dimethoxyphenyl)-piperazin-2-one prepared in accordance with Example 1 are boiled under reflux for 12 hours with 27.8 g (0.22 mol) of benzyl chloride and 23.3 g (0.22 mol) of sodium carbonate in 500 ml of chlorobenzene.

After cooling, the reaction mixture is filtered with suction, the filtrate is evaporated in vacuo, the residue is taken up in methylene chloride and the solution is extracted by shaking thoroughly with water and the methylene chloride is evaporated. The residue is stirred with a little ether, the mixture is filtered with suction again and the filter residue is dried.

Yield: 44 g≈67.5% of theory (molecular weight 326),

Melting point: 167°–168° C.

The hydrochloride, melting point 231°–234° C., is obtained by dissolving the substance in a little alcohol and adding ether saturated with hydrogen chloride.

EXAMPLE 3

3-(3,4-dimethoxyphenyl)-4-acetylpiperazin-2-one 23.6 1 g (0.1 mol) of the 3-(3,4-dimethoxyphenyl)-piperazin-2-one prepared in accordance with Example 1 are introduced into 100 ml of acetic anhydride.

After the exothermic reaction has subsided, the mixture is stirred for a further 2 hours at room temperature and concentrated in vacuo, and the residue is washed first with aqueous ammonia solution and then with water, and is taken up in methylene chloride. After drying, the solution is evaporated in vacuo and the residue is triturated with a little ether and filtered off with suction.

Yield: 20.1 g=72.3% of theory (molecular weight 278),
Melting point: 169°–170° C.

EXAMPLE 4

3-(3,4-dimethoxyphenyl)-4-carbonamidopiperazin-2-one 23.6 g (0.1 mol) of the 3-(3,4-dimethoxyphenyl)-piperazin-2-one prepared in accordance with Example 1 are stirred with 250 ml of water and 10 ml (0.1 mol) of 10N hydrochloric acid, and 8.1 g (0.1 mol) of potassium cyanate, dissolved in 20 ml of water, are added dropwise. The mixture is stirred for 8 hours at room temperature and then filtered with suction. The filter residue is washed with water and boiled up with 150 ml of ethanol, it is cooled and filtered off with suction again and dried.

Yield: 20 g=78.7% of theory (molecular weight 254),
Melting point: 196°–199° C.

EXAMPLE 5

3-(3,4-dimethoxyphenyl)-4-formylpiperazin-2-one 23.6 g (0.1 mol) of 3-(3,4-dimethoxyphenyl)-piperazin-2-one, prepared in accordance with Example 1, are heated at 110° C. with 150 ml of methyl formate for 3 hours in an autoclave. The residue remaining after the mixture has been concentrated in vacuo is triturated with ether, filtered off with suction and dried.

Yield: 24 g=91% of theory (molecular weight 264),
Melting point: 125°–127° C.

EXAMPLE 6

3-(3,4-dimethoxyphenyl)-4-carbonamidomethylpiperazin-2-one 10 g (0.03 mol) of 3-(3,4-dimethoxyphenyl)-4-carbomethoxymethylpiperazin-2-one, 180 ml of ethanol and 20 ml of liquid ammonia are heated at 70°–80° C. for 12 hours in an autoclave. After cooling, the product is filtered off with suction, washed with ethanol and dried.

Yield: 5.3 g=60% of theory (molecular weight 293),
Melting point: 230°–231° C.

The starting material is prepared as follows: 23.6 g (0.1 mol) of 3-(3,4-dimethoxyphenyl)-piperazin-2-one (Example 1) and 12 g of methylchloroacetate in 150 ml of chlorobenzene are boiled under reflux for 12 hours in the presence of 11.7 g (0.11 mol) of sodium carbonate. The reaction mixture is then evaporated, the residue is taken up in water/methylene chloride, the organic layer is separated off and evaporated and the residue remaining is triturated with ether and filtered off with suction.

Yield: 19.7 g≈64% of theory (molecular weight 308),
Melting point: 116°–118° C.

EXAMPLE 7

3-(3,4-dimethoxyphenyl)-4-aminoacetylpiperazin-2-one hydrochloride 7.5 g (0.024 mol) of 3-(3,4-dimethoxyphenyl)-4-chloroacetylpiperazin-2-one, 400 ml of methanol and 20 ml of liquid ammonia are heated at 80°–90° C. for 12 hours in an autoclave. After cooling, the reaction mixture is evaporated in vacuo, the residue is dissolved in a little methanol, and the solution is filtered and evaporated again.

Yield: 5.8 g=73% of theory (molecular weight 329),
Melting point: 140° C. (decomposition).

The starting material is prepared as follows: a solution of 11.5 g (0.1 mol) of chloroacetyl chloride in 50 ml of chloroform is added, while cooling, to 23.6 g (0.1 mol) of 3-(3,4-dimethoxyphenyl)-piperazin-2-one (Example 1), 150 ml of chloroform and 10.1 g of triethylamine. The mixture is stirred for a further hour at room temperature and is concentrated in vacuo, the residue is taken up in aqueous potassium carbonate solution, and the solution is extracted by shaking with ethyl acetate. Distilling off the ethyl acetate gives 17.5 g≈56% of theory of 3-(3,4-dimethoxyphenyl)-4-chloroacetylpiperazin-2-one.

Molecular weight: 312.5,
Melting point: 102°–106° C.

EXAMPLE 8

3-(3,4-dimethoxyphenyl)-4-morpholinoacetylpiperazin-2-one 7.8 g of the 3-(3,4-dimethoxyphenyl)-4-chloroacetyl-piperazin-2-one prepared in accordance with Example 7, 50 ml of toluene and 4.5 g (0.05 mol) of morpholine are boiled under reflux for 3 hours. The reaction mixture is then concentrated in vacuo, an aqueous solution of potassium carbonate is added to the residue and the mixture is extracted by shaking with methylene chloride. The organic phase is separated off and the methylene chloride is removed by evaporation.

Yield: 6 g≈66% of theory (molecular weight 363),
Melting point: 136°–137° C.

EXAMPLE 9

1-methyl-3-(3,4-dimethoxyphenyl)-4-benzylpiperazin-2-one 32.6 g (0.1 mol) of 3-(3,4-dimethoxyphenyl)-4-benzyl-piperazin-2-one, prepared in accordance with Example 2, are dissolved in 150 ml of dimethyl sulphoxide, the solution is stirred with 12.3 g (0.11 mol) of potassium tert.-butylate for 15 minutes at room temperature and 15.6 g (0.11 mol) of methyl iodide are added, while cooling. After 1 hour the dimethyl sulphoxide is distilled off in vacuo, water is added to the residue and the mixture is rendered alkaline and extracted by shaking with ethyl acetate. The organic phase is separated off and the solvent is removed by distillation, to leave the compound in the form of a viscous oil.

Yield: 35.4 g. Dissolving the product in isopropanol and adding an equivalent quantity of naphthalene-1,5-disulphonic acid gives the naphthalene-disulphonate, melting point 162°–165° C.

EXAMPLE 10

1-carbonamidomethyl-3-(3,4-dimethoxyphenyl)-4-benzylpiperazin-2-one 17.5 g (0.044 mol) of 1-carbomethoxymethyl-3-(3,4-dimethoxyphenyl)-4-benzylpiperazin-2-one are heated with 150 ml of ethanol and 50 ml of liquid ammonia at 70°–80° C. for 12 hours in an autoclave. After the reaction product has been concentrated in vacuo, the residue is taken up in ethyl acetate and the solvent is removed by distillation. Triturating the residue with ether and filtering off with suction gives 9.5 g of crude product, which is recrystallized from 70 ml of ethanol.

Yield: 6 g≈36% of theory (molecular weight 382),
Melting point: 206°–208° C.

The 1-carbomethoxymethyl-3-(3,4-dimethoxyphenyl)-4-benzylpiperazin-2-one used as the starting material is prepared as follows: 40 g (0.12 mol) of 3-(3,4-dimethoxyphenyl)-4-benzylpiperazin-2-one, prepared in accordance with Example 2, are introduced into a solution of 20 g (0.18 mol) of potassium tert.-butylate in 250 ml of dimethyl sulphoxide. The mixture is stirred for 15 minutes at room temperature, 19.5 g (0.18 mol) of methylchloroacetate are added dropwise and stirring is continued for 6 hours at 40°–50° C. After the dimethyl sulphoxide has been removed by distillation in vacuo, a solution of potassium carbonate in water is added to the residue and the mixture is extracted by shaking with ethyl acetate. The organic phase is separated off and the ethyl acetate is removed by distillation, to leave 43.5 g of a viscous oil, which is used without further purification.

EXAMPLE 11

1-carbonamidomethyl-3-(3,4-dimethoxyphenyl)-piperazin-2-one tartrate 6.5 g (0.02 mol) of 1-carbonamidomethyl-3-(3,4-dimethoxyphenyl)-4-benzylpiperazin-2-one, prepared in accordance with Example 10, are dissolved in 80 ml of glacial acetic acid and are hydrogenated at room temperature in the presence of a palladium/charcoal catalyst until saturation is reached. The reaction mixture is then freed from the catalyst and is concentrated in vacuo, the residue is rendered alkaline with aqueous potassium carbonate solution, the oil which is precipitated is dissolved in dimethoxyethane and the 1-carbonamidomethyl-3-(3,4-dimethoxyphenyl)piperazin-2-one is precipitated as the tartrate by adding tartaric acid.

Yield: 3.4 g≈38% of theory (molecular weight 443).

EXAMPLE 12

1-[4-(2-methoxyphenyl)-piperazine-1-carbomethyl]-3-(3,4-dimethoxyphenyl)-4-benzylpiperazin-2-one sulphate 17.1 g (0.043 mol) of 1-carbomethoxymethyl-3-(3,4-dimethoxyphenyl)-4-benzylpiperazin-2-one, prepared in accordance with Example 10, 100 ml of glycol monomethyl ether and 9.1 g (0.047 mol) of 1-(2-methoxyphenyl)-piperazine are boiled under reflux for 10 hours. The reaction mixture is concentrated in vacuo, the residue is stirred with water and ethyl acetate, the ethyl acetate phase is separated off, dried and concentrated and the oil which remains is dissolved in a little ethanol. The abovementioned sulphate is precipitated by adding a solution of 1.7 g of sulphuric acid in ethanol. It is filtered off with suction and washed with ether.

Yield: 6.6 g=23% of theory (molecular weight 654),
Melting point: 215°–217° C.

EXAMPLE 13

3-(4-fluorophenyl)-piperazin-2-one 24 g (0.125 mol) of 3-(4-fluorophenyl)-5,6-dihydro-2(1H)-pyrazinone are hydrogenated and worked up as described in Example 1, and the product is recrystalized from ethyl acetate.

Yield: 15 g=61.8% of theory (molecular weight 194),
Melting point: 105°–108° C.

EXAMPLE 14

3-(4-fluorophenyl)-4-benzylpiperazin-2-one 25 g (0.129 mol) of 3-(4-fluorophenyl)-piperazin-2-one, prepared in accordance with Example 13, are alkylated with 18.1 g (0.143 mol) of benzyl chloride, as described in Example 2.

Yield: 24.3 g=66.3% of theory (molecular weight 284),
Melting point: 170°–172° C.

EXAMPLE 15

3-(4-fluorophenyl)-4-formylpiperazin-2-one 10 g (0.051 mol) of 3-(4-fluorophenyl)-piperazin-2-one, prepared in accordance with Example 13, are acylated by heating with methyl formate, as described in Example 5.

Yield: 6 g=53% of theory (molecular weight 222),
Melting point: 120°–123° C.

If acetic anhydride is used as the acylation component and the reaction is carried out analogously to Example 3, 3-(4-fluorophenyl)-4-acetylpiperazin-2-one is obtained in a 57% yield, molecular weight 236, melting point 139°–140° C.

EXAMPLE 16

3-(2-thienyl)-piperazin-2-one 22.2 g (0.123 mol) of 3-(2-thienyl)-5,6-dihydro-2(1H)-pyrazinone are hydrogenated and worked up, as described in Example 1.

Yield: 17 g of 3-(2-thienyl)-3-piperazin-2-one≈75.9% of theory (molecular weight 182),
Melting point: 118° C.

EXAMPLE 17

3-(2-thienyl)-4-formylpiperazin-2-one 9.1 g (0.05 mol) of 3-(2-thienyl)-piperazin-2-one (Example 16) are reacted with methyl formate, as described in Example 5.

Yield: 8 g of 3-(2-thienyl)-4-formylpiperazin-2-one, 76% of theory (molecular weight 210),
Melting point: 127°–129° C.

The following compounds were prepared analogously to Example 3, using the corresponding acylating agents:

Using acetic anhydride as the acylating agent: 3-(2-thienyl)-4-acetylpiperazin-2-one, yield: 81% of theory, melting point: 144°–146° C.

Using nicotinic anhydride: 3-(2-thienyl)-4-nicotinoyl-piperazin-2-one, yield: 71% of theory, melting point: 240°–241° C. (hydrochloride).

Using trimethoxybenzoyl chloride: 3-(2-thienyl)-4-(3,4,5-trimethoxybenzoyl)-piperazin-2-one, yield: 63% of theory, melting point: 164°–165° C.

Using 4-nitrobenzoyl chloride: 3-(2-thienyl)-4-(4-nitrobenzoyl)-piperazin-2-one, yield: 83% of theory, melting point: 204° C.

Catalytic reduction of the nitro group, using the conditions described in Example 1, gives 3-(2-thienyl)-4-(4-aminobenzoyl)-piperazin-2-one, yield: 70% of theory, melting point: 181°–182° C.

EXAMPLE 18

1-carboethoxymethyl-3-(2-thienyl)-4-acetylpiperazin-2-one 12 g (0.053 mol) of 3-(2-thienyl)-4-acetylpiperazin-2-one, prepared in accordance with Example 17, are stirred with 6.6 g (0.059 mol) of potassium tert.-butylate in 100 ml of dimethyl sulphoxide. After removing 10 ml of dimethyl sulphoxide by distillation in vacuo, 6.4 g (0.059 mol) of ethylchloroacetate are added dropwise at room temperature and the mixture is stirred for a further 12 hours. The dimethyl sulphoxide is removed by evaporation in vacuo, the residue is stirred with water and taken up in ethyl acetate, and the organic phase is separated off. Distilling off the ethyl acetate gives 13.8 g of the title product, 88% of theory (molecular weight 296), in the form of a viscous oil.

EXAMPLE 19

1-carbonamidomethyl-3-(2-thienyl)-4-acetylpiperazin-2-one 13.9 g (0.047 mol) of 1-carbomethoxymethyl-3-(2-thienyl)-4-acetylpiperazin-2-one, prepared in accordance with Example 18, are dissolved in 180 ml of ethanol and heated at 80°–90° C. with 20 ml of liquid ammonia for 12 hours in an autoclave. The reaction mixture is evaporated in vacuo, the residue is extracted by boiling with methanol and active charcoal, and the methanol solution is filtered and evaporated.

Yield: 6 g, 45.4% of theory (molecular weight 281), Melting point: 162°–165° C.

EXAMPLE 20

3-(2-thienyl)-4-carbonamidopiperazin-2-one 9.1 g (0.05 mol) of 3-(2-thienyl)-piperazin-2-one, prepared in accordance with Example 16, are reacted with potassium cyanate and worked up, as described in Example 4.

Yield: 8.8 g, 78% of theory (molecular weight 225), Melting point: 219°–222° C.

EXAMPLE 21

3-(2-thienyl)-4-chloroacetylpiperazin-2-one 18.2 g (0.1 mol) of 3-(2-thienyl)-piperazin-2-one, prepared in accordance with Example 16, are dissolved in 150 ml of chloroform and 11.1 g (0.11 mol) of triethylamine and 12.4 g (0.11 mol) of chloroacetyl chloride are added. The mixture is stirred for 4 hours at room temperature, the reaction solution is concentrated in vacuo and the residue is stirred with water and ethyl acetate. The ethyl acetate solution is separated off, dried and evaporated in vacuo.

Yield: 19.7 g, 76% of theory (molecular weight 259), of a viscous oil.

EXAMPLE 22

Reacting the compound obtained in Example 21 with ammonia or morpholine, as described in Example 7, gives 3-(2-thienyl)-4-aminoacetylpiperazin-2-one: melting point: 130° C. (decomposition), or 3-(2-thienyl)-4-(morpholinomethylcarbonyl)-piperazin-2-one: melting point: 144°–146° C., respectively.

EXAMPLE 23

3-(2-thienyl)-4-(3-chlorophenylaminocarbonyl)-piperazin-2-one 5.5 g (0.03 mol) of 3-(2-thienyl)-piperazin-2-one, prepared in accordance with Example 16, are dissolved in 60 ml of methylene chloride, 4.6 g (0.03 mol) of 3-chlorophenyl isocyanate, dissolved in 20 ml of methylene chloride, are added dropwise and the mixture is stirred for a further 5 hours at room temperature. The reaction product which has been precipitated is filtered off with suction, washed with methylene chloride and dried.

Yield: 8.2 g, 81% of theory (molecular weight 335.5), Melting point: 173°–175° C.

EXAMPLE 24

3-(2-thienyl)-4-carbomethoxymethylpiperazin-2-one 18.2 g (0.1 mol) of 3-(2-thienyl)-piperazin-2-one, prepared in accordance with Example 16, are reacted with methyl chloroacetate and worked up, as described in Example 6.

Yield: 18.6 g, 73% of theory (molecular weight 254), Melting point: 119°–123° C.

EXAMPLE 25

3-(2-thienyl)-4-carbonamidomethylpiperazin-2-one 8.9 g (0.035 mol) of the 3-(2-thienyl)-4-carbomethoxymethylpiperazin-2-one, prepared in accordance with Example 24 are reacted with ammonia, as described in Example 6.

Yield: 4.7 g = 56% of theory (molecular weight 239), Melting point: 215°–217° C.

Using morpholine as the reactant instead of ammonia gives 3-(2-thienyl)-4-morpholinocarbonylmethylpiperazin-2-one, melting point: 190°–193° C.

EXAMPLE 26

3-(2-thienyl)-4-dimethylaminosulphonylpiperazin-2-one 9.1 g (0.05 mol) of 3-(2-thienyl)-piperazin-2-one, prepared in accordance with Example 16, are mixed with a solution of 6.1 g (0.06 mol) of triethylamine in 100 ml of chloroform, and 8.6 g (0.06 mol) of dimethylaminosulphonyl chloride are added dropwise slowly. The reaction mixture is then stirred for a further 6 hours at room temperature and evaporated in vacuo, the residue is stirred with water and the mixture is extracted by shaking with ethyl acetate. The ethyl acetate phase is separated off, the ethyl acetate is removed by distillation and the residue is recrystallised from ethanol.

Yield: 9.7 g ≈ 67% of theory (molecular weight 289), Melting point: 134°–136° C.

EXAMPLE 27

3-(2-thienyl)-4-hydroxyethylpiperazin-2-one tartrate 18.2 g (0.1 mol) of 3-(2-thienyl)-piperazin-2-one, prepared in accordance with Example 16, are stirred with 13.2 g (0.3 mol) of ethylene oxide in 180 ml of ethanol at 60° C. for 24 hours in an autoclave. The reaction mixture is concentrated in vacuo, the residue is dissolved in ethyl acetate and a hot solution of tartaric acid in ethyl acetate is added to the solution. The tartrate which is precipitated is filtered off with suction, washed with ethyl acetate and dried.

Yield: 28 g ≈ 74% of theory (molecular weight 376), Melting point: 60°–63° C.

EXAMPLE 28

3-(2-thienyl)-4-(4'-chlorophenoxymethylcarbonyloxyethyl)-piperazin-2-one hydrochloride 18.1 g (0.08 mol) of 3-(2-thienyl)-4-hydroxyethylpiperazin-2-one, prepared in accordance with Example 27, are dissolved in 160 ml of chloroform and acylated with 10.1 g (0.1 mol) of triethylamine and 20.5 g (0.1 mol) of 4-chlorophenoxyacetyl chloride. The mixture is stirred for a further 4 hours at room temperature and evaporated, and the residue is extracted by shaking with ethyl acetate. The ethyl acetate extract is dried with sodium sulphate, and the compound is precipitated as the hydrochloride by adding hydrochloric acid in ether.

Yield: 28 g≈65% of theory (molecular weight 431), Melting point: 211°–213° C.

EXAMPLE 29

3-(2-thienyl)-4-benzylpiperazin-2-one 54.6 g (0.3 mol) of 3-(2-thienyl)-piperazin-2-one, prepared in accordance with Example 16, are reacted with 41.7 g (0.33 mol) of benzyl chloride, as described in Example 2.

Yield: 61.7 g≈75.6% of theory (molecular weight 272),

Melting point: 161° C. (decomposition).

The following compounds were obtained analogously using the corresponding substituted benzyl chlorides:

3-(2-thienyl)-4-(4-chlorobenzyl)-piperazin-2-one,
yield: 78% of theory,
melting point: 191°–193° C.

3-(2-thienyl)-4-(2-chlorobenzyl)-piperazin-2-one,
yield: 70% of theory,
melting point: 156° C.

3-(2-thienyl)-4-(3,4-dichlorobenzyl)-piperazin-2-one,
yield: 80% of theory,
melting point: 127° C.

3-(2-thienyl)-4-(4-methoxybenzyl)-piperazin-2-one,
yield: 80% of theory,
melting point: 216°–218° C.

Using 3,4-dimethoxyphenethyl bromide analogously as the alkylating agent gives 3-(2-thienyl)-4-(3,4-dimethoxyphenethyl)-piperazin-2-one in a yield of 68% of theory, melting point of naphthalene-1,5-disulphonate: 261°–262° C.

EXAMPLE 30

3-(3-indolyl)-piperazin-2-one 21.3 g (0.1 mol) of 3-(3-indolyl)-5,6-dihydro-2(1H)-pyrazinone are hydrogenated, as described in Example 1.

Yield: 18 g≈84% of theory (molecular weight 215), Melting point: 152°–155° C.

EXAMPLE 31

3-(3-indolyl)-4-formylpiperazin-2-one 21.5 g (0.1 mol) of 3-(3-indolyl)-piperazin-2-one (Example 30) are formylated with methylformate, as described in Example 5.

Yield: 19.5 g=80% of theory (molecular weight 243), Melting point: 260°–262° C.

EXAMPLE 32

3-(3-indolyl)-4-benzylpiperazin-2-one 21.5 g (0.1 mol) of 3-(3-indolyl)-piperazin-2-one, prepared in accordance with Example 30, are alkylated with benzyl chloride as described in Example 2.

Yield: 27 g≈88% of theory (molecular weight 305), Melting point: 232°–234° C.

EXAMPLE 33

3-(1-methylindol-3-yl)-5,6-dihydro-2(1H)-pyrazinone 240 g (4 mols) of 1,2-diaminoethane, dissolved in 4,000 ml of ethanol, are initially taken and 462 g (2 mols) of ethyl 1-methylindolyl-3-glyoxylate are added dropwise at room temperature. The mixture is then heated at 70° C. for 2 hours. After the ethanol has been removed by evaporation, the residue is stirred in 5 liters of water and the pH is adjusted to 1 with concentrated hydrochloric acid. The undissolved by-product is filtered off, the acid filtrate is rendered alkaline and the precipitate formed is filtered off with suction.

Yield: 335 g≈73.8% of theory (molecular weight 227),

Melting point: 176°–179° C.

EXAMPLE 34

3-(1-methylindol-3-yl)-piperazin-2-one 22.7 g (0.1 mol) of 3-(1-methylindol-3-yl)-5,6-dihydro-2(1H)-pyrazinone, prepared in accordance with Example 33, are hydrogenated, as described in Example 1.

Yield: 19.4 g≈85% of theory (molecular weight 229), Melting point: 163°–166° C.

EXAMPLE 35

3-(1-methylindol-3-yl)-4-formylpiperazin-2-one 22.9 g (0.1 mol) of 3-(1-methylindol-3-yl)-piperazin-2-one, prepared in accordance with Example 34, are reacted with methyl formate, as described in Example 5.

Yield: 19 g≈78% of theory (molecular weight 243), Melting point: 216°–218° C.

EXAMPLE 36

3-(1-methylindol-3-yl)-4-[3-(2-ethoxyphenyl)-2-hydroxyprop-1-yl]-piperazin-2-one 11.5 g (0.05 mol) of 3-(1-methylindol-3-yl)-piperazin-2-one, prepared in accordance with Example 34, are dissolved in 100 ml of isoamyl alcohol, 9.7 g (0.05 mol) of 3-(2-ethoxyphenoxy)-1,2-epoxypropane are added and the mixture is stirred for 5 hours at 120° C. The reaction mixture is evaporated in vacuo, the residue is dissolved in ethyl acetate, and the hydrochloride is precipitated by adding hydrochloric acid in ether. The product is filtered off with suction and dried.

Yield: 16 g=72% of theory (molecular weight 441.5), Melting point: 148°–151° C.

EXAMPLE 37

3-[1-(4-chlorobenzyl)-indol-3-yl]-piperazin-2-one 164 g (0.68 mol) of 1-(4-chlorobenzyl)-indole are dissolved in 1,400 ml of ether and 119 g (0.935 mol) of oxalyl chloride are added dropwise. The mixture is stirred for a further 8 hours at room temperature and is filtered with suction and the residue is stirred in 800 ml of ethanol at 60° C. for 1 hour. After concentrating the mixture and filtering with suction, the filter residue is recrystallised from isopropanol.

Yield: 162.2 g≈70% of theory of ethyl 1-(4-chlorobenzyl)-indol-3-yl-glyoxylate (molecular weight 341), melting point: 123°–125° C.

136.4 g (0.4 mol) of the ethyl 1-(4-chlorobenzyl)-indol-3-yl-glyoxylate prepared in accordance with the above instructions are reacted with ethylenediamine and worked up, as described in Example 33. This gives 93 g≈77% of theory of 3-[1-(4-chlorobenzyl)-indol-3-yl]-5,6-dihydro-2(1H)-pyrazinone, melting point: 185°–186° C.

90 g of the product thus obtained are hydrogenated and worked up analogously to the instructions in Example 1. This gives 74 g=82% of theory of 3-[1-(4-chlorobenzyl)-indol-3-yl]-piperazin-2-one, melting point: 195° C.

EXAMPLE 38

Carrying out the process of Example 37 analogously, starting from the same quantity of 1-(2-chlorobenzyl)-indole, gives, in an overall yield of 45%, 3-[1-(2-chlorobenzyl)-indol-3-yl]-piperazin-2-one, melting point: 181° C.

EXAMPLE 39

3-(2-phenylindol-3-yl)-piperazin-2-one

The compound is obtained in a yield of 82% by hydrogenating 3-(2-phenylindol-3-yl)-5,6-dihydro-2(1H)-pyrazinone.

Melting point: 165° C. (decomposition).

The 3-(2-phenylindol-3-yl)-5,6-dihydro-2(1H)-pyrazinone required as the starting material is prepared from ethyl 2-phenyl-indol-3-yl-glyoxylate and ethylenediamine by the method described in Example 33.

Yield: 76% of theory,
Melting point: 300° C.

The ethyl 2-phenylindol-3-yl glyoxylate required for the reaction is obtained in a yield of 72% of theory from 2-phenyl-indol, oxalyl chloride and ethanol, as described in Example 37.

Melting point: 174°–176° C.

EXAMPLE 40

1-methyl-3-(1-methylindol-3-yl)-4-formylpiperazin-2-one 14 g (0.058 mol) of 1-methyl-3-(1-methylindol-3-yl)-5,6-dihydro-2(1H)-pyrazinone are dissolved in 200 ml of methanol, 6.6 g (0.17 mol) of sodium borohydride are added, and the mixture is stirred for 20 hours at 60° C. The residue remaining after the methanol has been removed by evaporation is heated with 200 ml of methyl formate at 100°–110° C. for 10 hours in an autoclave, and the mixture is then evaporated. The residue remaining after evaporation is recrystallised from a mixture of glycol monomethyl ether and ethanol.

Yield: 11 g≈70% of theory (molecular weight 271),
Melting point: 163°–165° C.

The 1-methyl-3-(1-methylindol-3-yl)-5,6-dihydro-2(1H)-pyrazinone required as the starting material is prepared as follows: 45.5 g (0.2 mol) of 3-(1-methylindol-3-yl)-5,6-dihydro-2(1H)-pyrazinone, prepared in accordance with Example 33, are dissolved in 400 ml of dimethylformamide, 5.3 g (0.22 mol) of sodium hydride are introduced, the mixture is stirred for 4 hours at 60° C., 27.8 g (0.22 mol) of dimethyl sulphate are added dropwise and the mixture is stirred for 20 hours at 60° C. The compound which is precipitated by dilution with water is recrystallised from methanol.

Yield: 22 g≈46% of theory (molecular weight 241),
Melting point: 165°–168° C.

EXAMPLE 41

3-(1-methyl-5-methoxyindol-3-yl)-piperazin-2-one

The compound is prepared by hydrogenating 3-(1-methyl-5-methoxy-indol-3-yl)-5,6-dihydro-2(1H)-pyrazinone, as described in Example 1.

Yield: 78% of theory,
Melting point: 155°–157°.

The starting material required for this preparation can be prepared as follows: 13.1 g (0.05 mol) of ethyl 1-methyl-5-methoxyindol-3-yl-glyoxylate are reacted with 15 g (0.25 mol) of 1,2-diaminoethane, as described in Example 33.

Yield: 8 g≈62% of theory (molecular weight 257),
Melting point: 225°–227° C.

The ethyl 1-methyl-5-methoxyindol-3-yl glyoxylate required is prepared in the following manner: 34.2 g (0.23 mol) of oxalyl chloride are added to 29 g (0.18 mcl) of 1-methyl-5-methoxyindole in 300 ml of ether, and the mixture is stirred for 4 hours at room temperature. The mixture is filtered with suction and the residue is stirred in 300 ml of ethanol at 60° C. for 3 hours. The mixture is then filtered with suction and the filter residue is recrystallised from isopropanol.

Yield: 32 g=68% of theory (molecular weight 261),
Melting point: 121°–123° C.

EXAMPLE 42

3-(4-methoxyphenyl)-piperazin-2-one 20.4 g (0.1 mol) of 3-(4-methoxyphenyl)-5,6-dihydro-2(1H)-pyrazinone are hydrogenated, as described in Example 1.

Yield: 17.3 g=84% of theory (molecular weight 206),
Melting point: 140°–142° C.

EXAMPLE 43

3-[4-(2-methoxyethoxy)-phenyl]-piperazin-2-one 55.2 g (0.414 mol) of aluminium chloride, dissolved in 150 ml of nitrobenzene, are initially taken and 36.8 g (0.27 mol) of oxalic acid ethyl ester-chloride followed by 63 g (0.414 mol) of 4-(2-methoxyethoxy)-benzene are added dropwise, while cooling. The mixture is stirred for a further 10 hours and poured into ice water and the mixture is extracted by shaking with ether. The ether layer is separated off, washed first with sodium bicarbonate solution and then with water, and dried. The solution is evaporated in vacuo and the residue is distilled. Boiling point: 150° C./0.1 mbar, yield: 29 g of ethyl 4-(2-methoxyethoxy)phenyl-glyoxylate=28% of theory (molecular weight 252).

27.7 g (0.11 mol) of the ethyl 4-(2-methoxyethoxy)-phenylglyoxylate thus prepared are reacted with 1,2-diaminoethane, as described in Example 33. This gives 17 g=62% of theory of 3-[4-(2-methoxyethoxy)-phenyl]-5,6-dihydro-2(1H)-pyrazinone (molecular weight 248), melting point: 130°–132° C.

The product thus obtained is then hydrogenated, as described in Example 1.

Yield: 13.9 g=82% of theory of 3-[4-(2-methoxyethoxy)-phenyl]-piperazin-2-one,
Melting point: 96°–97° C.

EXAMPLE 44

3-(4-diethylaminoethoxyphenyl)-piperazin-2-one 54 g (0.28 mol) of ethyl 4-hydroxyphenyl glyoxylate are dissolved in 500 ml of dimethylformamide, 46 g (0.336 mol) of potassium carbonate and 45 g (0.336 mol) of diethylaminoethyl chloride are added, and the mixture is stirred for 12 hours at room temperature. The reaction mixture is then poured into 3 liters of water, the mixture is extracted by shaking with ethyl acetate, and the ethyl acetate phase is separated off, dried and evaporated in vacuo. The oily substance which remains is dissolved in 1,000 ml of ethanol and stirred with 16 g (0.26 mol) of ethylenediamine for 16 hours at room temperature. The reaction mixture is then concentrated in vacuo, the residue is stirred with water and extracted by shaking with ethyl acetate, and the ethyl acetate phase is again evaporated. The product crystallises on triturating the residue with petroleum ether.

Yield: 49.5 g=61% of theory (molecular weight 290),
Melting point: 72°–75° C.

45 g of the 3-(4-diethylaminoethoxyphenyl)-5,6-dihydro-2(1H)-pyrazinone thus obtained are hydrogenated, as described in Example 1.

Yield: 35.4 g=79% of theory (molecular weight 292),
Melting point: 82°–83° C.

EXAMPLE 45

3-(4-diethylaminoethoxyphenyl)-4-formylpiperazin-2-one 29.2 g (0.1 mol) of 3-(4-diethylaminoethoxyphenyl)-piperazin-2-one are acylated by boiling with ethyl formate and the mixture is worked up, as described in Example 5. After being worked up, the product is precipitated as the salt of naphthalene-1,4-disulphonic acid by adding this acid.

Yield: 39.4 g=85% of theory,
Melting point: 150°–153° C.

EXAMPLE 46

3-(3-pyridyl)-piperazin-2-one 66 g (0.11 mol) of diaminoethane in 600 ml of ethanol are initially taken and 17.9 g (0.1 mol) of pyrid-3-yl glyoxylate are added dropwise slowly. The mixture is stirred at room temperature for a further 6–8 hours and is then hydrogenated at 90° C. and under a hydrogen pressure of 80 bar, with the addition of Raney nickel as catalyst, until saturation is reached. The catalyst is filtered off with suction, the filtrate is evaporated to dryness in vacuo and the residue is recrystallised from isopropanol.

Yield: 10.9 g=62% of theory,
Melting point: 150°–152° C., molecular weight 176.

EXAMPLE 47

Tablets can be prepared according to the following formulation:

| | |
|---|---|
| Active compound | 2 mg |
| Lactose | 60 mg |
| Cornstarch | 30 mg |
| Soluble starch | 4 mg |
| Magnesium stearate | 4 mg |
| | 100 mg |

EXAMPLE 48

Sugar-coated pills can be prepared according to the following formulation:

| | |
|---|---|
| Active compound | 1 mg |
| Cornstarch | 100 mg |
| Lactose | 60 mg |
| Sec. calcium phosphate | 30 mg |
| Soluble starch | 3 mg |
| Magnesium stearate | 2 mg |
| Colloidal silicic acid | 4 mg |
| | 200 mg |

EXAMPLE 49

Soft gelatine capsules, containing 5 mg of active compound per capsule can be prepared according to the following formulation:

| | per capsule |
|---|---|
| Active compound | 5 mg |
| Mixture of triglycerides obtained by fractionation from coconut oil | 150 mg |
| Contents of capsule | 155 mg |

EXAMPLE 50

Injection solution, containing 1 mg of active compound per ml can be prepared according to the following formulation:

| | per ml |
|---|---|
| Active compound | 1.0 mg |
| Polyethylene glycol 400 | 0.3 ml |
| Sodium chloride | 2.7 mg |
| Water for injection purposes | ad 1 ml |

EXAMPLE 51

Emulsions, containing 3 mg of active compound per 5 ml can be prepared according to the following formulation:

| | per 100 ml of emulsion |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2.0 g |
| Flavouring substance | q.s. |
| Water (demineralised or destilled) | ad 100 ml |

The compounds of the invention are examined in three different test procedures A, B and C which, each by itself but, in particular, in combination with one another, show the efficacy and the value of the substances.

(A) "Nitrite Hypoxia"

In this test a cerebral hypoxia is generated in mice with $NaNO_2$ (250 mg/kg s) using the Gibson and Blass method (J. Neurochem. 27, 1976), the hypoxia resulting in the death of the test animals. The test determines whether the survival time can be influenced by premedication using the test substance.

Minimum active dosage is the dosage resulting in a significant prolongation of the survival time (t—test) of the test animals.

(B) "Nitrogen Hypoxia"

To determine the impact of nitrogen respiration on the electric activity of the brain rats are used having chronically-implanted electrodes measuring the electroencephalogram (EEG).

One hour after injection of the control substance and the test substance the animals under hexobarbital anesthesia are subjected to nitrogen respiration with EEG control. Hypoxia tolerance is the time interval between the beginning of the respiration and the complete disappearance of electric activity (isoelectric EEG). A further respiration of short duration with nitrogen and subsequently with air usually results in the death of all control animals. The minimum active dosage of a preparation is the dosage that causes a significant prolongation of the hypoxia tolerance (t—test) and/or significantly decreases the lethality (chi-square test).

(C) "Passive Avoidance"

The test apparatus used is a bright/dark box with an electrifiable bottom grating in its dark portion. 90 minutes after injection of the control substance and the test substance inexperienced male mice are treated with scopolamine hydrobromide (3 mg/kg i.p.). 5 minutes later the mice are placed into the bright portion of the box. When getting into the dark section of the box they are given an electric shock which is disagreeable to them. After 24 hours each mouse is placed once into the bright section of the test apparatus and the residence time is measured (maximum of 300 sec). The significant effect of the test substance in comparison with the control group is calculated using the median test.

The minimum active dosage of a preparation is the dosage resulting in a significant effect against scopolamine. The animals treated with an active dosage of a preparation and with scopolamine feature a long residence time just as the animals not treated with scopolamine, whereas those having been given a control injection and scopolamine are characterised by a short residence time.

Table I on page 41 shows that the compounds of the invention exhibit a completely new cerebral-protective profile over the known comparison substances as they are significantly effective in all three test models.

TABLE I

| Substance | | | Minimum active Dosage/mg/kg | | | |
|---|---|---|---|---|---|---|
| $R^1$ | $R^2$ | $R^3$ | Nitrite Hypoxia | Nitrogen Tolerance | Hypoxia Lethality | Passive Avoidance |
| 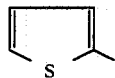 | H | H | 50 p.o. | 200 i.p. | 100 i.p. | 12.5 p.o. |
| 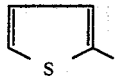 | $-CH_2-$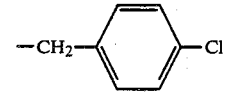$-Cl$ | H | 400 p.o. | 200 i.p. | 100 i.p. | 100 p.o. |
| Piracetam | | | 125 p.o. | 500 i.p. | — | — |
| Pyritinol | | | — | — | 200 i.p. | — |
| Meclofenoxat | | | 300 p.o. | — | — | — |
| Vincamin | | | — | — | — | 50 p.o. |

Further pharmacological data are apparent from the Tables II and III below.

The compounds of the invention show a strong action at a low dosage, a good compatibility and a low toxicity.

TABLE II

| Nitrite Hypoxia | | | |
|---|---|---|---|
| Substance | | | Minimum active |
| $R^1$ | $R^2$ | $R^3$ | Dosage [mg/kg] |
| 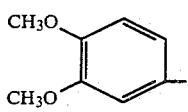 | $-CO-CH_3$ | $-CH_2-CO-NH_2$ | 100 p.o. |
|  | $-CH_2-$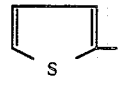 | $-CH_2-CO-N$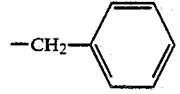$-$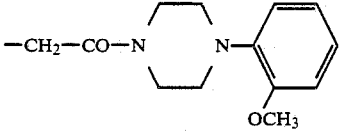$-OCH_3$ | 100 p.o. |
| " | $-CH_2-CH_2OH$ | H | 100 p.o. |
| " |  | H | 100 p.o. |

TABLE II-continued

| | Nitrite Hypoxia Substance | | Minimum active |
|---|---|---|---|
| R¹ | R² | R³ | Dosage [mg/kg] |
| " | −C(=O)−CH₂−NH₂ | H | 100 p.o. |
| " | −C(=O)−C₆H₄−NH₂ (para) | H | 100 p.o. |
| " | −C(=O)−C₆H₂(OCH₃)₃ (3,4,5-trimethoxy) | H | 100 p.o. |
| " | −C(=O)−NH−C₆H₄−Cl (meta) | H | 100 p.o. |
| " | −CH₂−C(=O)−NH₂ | H | 50 p.o. |
| " | −CH₂−C(=O)−N(morpholino) | H | 100 p.o. |
| " | −CH₂−C₆H₅ | H | 100 p.o. |
| " | −CH₂−C₆H₄−Cl (ortho) | H | 100 p.o. |
| " | −CH₂−C₆H₃(OCH₃)₂ (3,4-dimethoxy) | H | 25 p.o. |
| " | −CH₂−CH₂−O−C(=O)−CH₂−O−C₆H₄−Cl (para) | H | 100 p.o. |
| " | −CH₂−CH=CH₂ | H | 100 p.o. |
| " | −CH₂−C≡CH | H | 100 p.o. |
| 2-furyl | −H | H | 100 p.o. |
| " | −CH₂−CH₂−OH | H | 100 p.o. |

TABLE II-continued

Nitrite Hypoxia

| Substance | | | Minimum active |
|---|---|---|---|
| R¹ | R² | R³ | Dosage [mg/kg] |
| " | -CH₂-(2-Cl-phenyl) | H | 100 p.o. |
| 3-pyridyl | -H | H | 100 p.o. |
| 1-methylindol-3-yl | -H | H | 100 p.o. |
| " | -CH₂-CH₂-OH | H | 100 p.o. |
| " | -CHO | H | 100 p.o. |
| " | -C(=O)-CH₃ | H | 100 p.o. |
| " | -CH₂-(4-Cl-phenyl) | H | 100 p.o. |
| " | -CH₂-(3-Cl-phenyl) | H | 100 p.o. |
| " | -CH₂-(3,4-diCl-phenyl) | H | 100 p.o. |
| " | -CH₂-(2,4-diCl-phenyl) | H | 100 p.o. |
| Piracetam | | | 125 p.o. |
| Meclofenoxat | | | 300 p.o. |

TABLE III

Nitrogen Hypoxia

| Substance | | | Minimum active | Dosage/mg/kg |
|---|---|---|---|---|
| R¹ | R² | R³ | Hypoxia Tolerance | Lethality |
| 2-thienyl | -CH₂-CH₂-OH | H | 200 i.p. | 200 i.p. |

TABLE III-continued

| Substance | | | Nitrogen Hypoxia Minimum active | Dosage/mg/kg |
|---|---|---|---|---|
| $R^1$ | $R^2$ | $R^3$ | Hypoxia Tolerance | Lethality |
| " | —C(=O)NH₂ | H | 200 i.p. | 100 i.p. |
| " | —CH₂—C₆H₄—Cl | H | 200 i.p. | 100 i.p. |
| " | —CH₂—CH₂—O—C(=O)—CH₂—O—C₆H₄—Cl | H | 300 i.p. | 200 i.p. |
| indol-3-yl (NH) | —CHO | H | 200 i.p. | 200 i.p. |
| 1-methylindol-3-yl | —CH₂—C₆H₄—Cl | H | 200 i.p. | 200 i.p. |
| " | —CH₂—C₆H₃(Cl)(Cl) (2,3-dichloro) | H | 200 i.p. | 200 i.p. |
| Piracetam | | | 500 i.p. | — |
| Pyritinol | | | — | 200 i.p. |

What is claimed is:

1. A compound of the formula

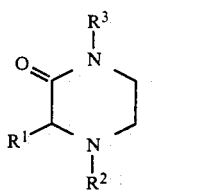
(I)

wherein
$R^1$ is phenyl, mono-, di- or tri-substituted phenyl, any substituent of substituted phenyl being independently selected from the group consisting of alkoxy having from 1 to 4 carbon atoms, fluoro, alkoxyalkyl having a total of from 2 to 6 carbon atoms or dialkylaminoalkoxy having a total of from 4 to 8 carbon atoms;

$R^2$ is hydrogen (—H); alkyl which has from 1 to 4 carbon atoms and is mono-substituted by alkoxycarbonyl having a total of from 2 to 5 carbon atoms, by amidocarbonyl or by substituted amidocarbonyl, the amino group of which is mono- or disubstituted by methyl or ethyl or is part of a piperidine, piperazine or morpholine nucleus; alkenyl having from 3 to 5 carbon atoms; alkynyl having from 3 to 5 carbon atoms; alkanoyl having from 1 to 4 carbon atoms; nicotinoyl; benzoyl which is mono-, di- or trisubstituted by alkoxy having 1 or 2 carbon atoms, or mono- or disubstituted by nitro or amino; amidosulfonyl; N-(mono- or di-)alkyl-substituted amidosulphonyl having a total of from 2 to 4 carbon atoms; a radical of formula III

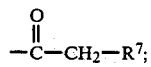
(III)

a radical of formula IV

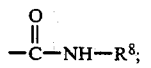
(IV)

or a radical of formula V

(V)

$R^3$ is hydrogen (—H), alkyl having from 1 to 4 carbon atoms, alkoxycarbonylmethyl having a total of from 3 to 6 carbon atoms, amidocarbonylmethyl, N-(mono- or di-)substituted amidocarbonylmethyl having a total of from 2 to 5 carbon atoms, or a radical of formula VII

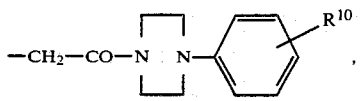

any substituent of N-substituted amidocarbonylmethyl being one of those indicated for N-substituted amidocarbonyl; $R^3$ being other than hydrogen (—H) when $R^2$ is hydrogen or when $R^1$ is unsubstituted phenyl;

$R^7$ is —NH$_2$, piperidin-1-yl, piperazin-1-yl, 4-(lower alkyl)-piperazin-1-yl or morpholino;

$R^8$ is hydrogen (—H), phenyl or chloro-substituted phenyl;

$R^9$ is hydrogen (—H), phenoxyacetyl or a radical of formula VI

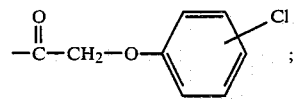

$R^{10}$ is hydrogen (—H) or alkoxy having 1 or 2 carbon atoms; or a physiologically-acceptable acid-addition salt thereof.

2. A compound according to claim 1 wherein $R^2$ is alkenyl having from 3 to 5 carbon atoms or alkynyl having from 3 to 5 carbon atoms.

3. A compound according to claim 1 wherein $R^3$ is alkyl having from 1 to 4 carbon atoms, alkoxycarbonylmethyl having a total of from 3 to 6 carbon atoms, amidocarbonylmethyl, N-(mono- or di-)substituted amidocarbonylmethyl having a total of from 2 to 5 carbon atoms, or a radical of formula VII

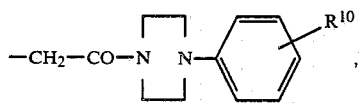

any substituent of N-substituted amidocarbonylmethyl being one of those indicated for N-substituted amidocarbonyl; and $R^{10}$ is hydrogen (—H) or alkoxy having 1 or 2 carbon atoms.

4. A compound according to claim 1 wherein
$R^1$ is mono-, di- or tri-substituted phenyl, any substituent of substituted phenyl being independently selected from the group consisting of alkoxy having from 1 to 4 carbon atoms, fluoro, alkoxyalkyl having a total of from 2 to 6 carbon atoms or dialkylaminoalkoxy having a total of from 4 to 8 carbon atoms;
$R^2$ is alkyl having from 1 to 4 carbon atoms; and
$R^3$ is hydrogen (—H) or alkyl having from 1 to 4 carbon atoms.

5. A compound according to one of claims 1 and 2 wherein $R^3$ is alkyl having from 1 to 4 carbon atoms, alkoxycarbonylmethyl having a total of from 3 to 6 carbon atoms, amidocarbonylmethyl, N-(mono- or di-)substituted amidocarbonylmethyl having a total of from 2 to 5 carbon atoms, or a radical of formula VII

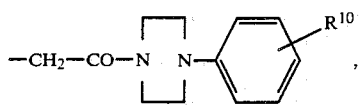

any substituent of N-substituted amidocarbonylmethyl being one of those indicated for N-substituted amidocarbonyl; and $R^{10}$ is hydrogen (—H) or alkoxy having 1 or 2 carbon atoms.

6. A compound of the formula

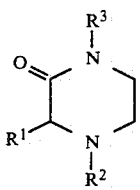

wherein
$R^1$ is 2-thienyl, 3-pyridyl or a radical of the formula

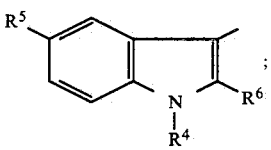

$R^2$ is hydrogen (—H); alkyl which has from 1 to 4 carbon atoms and is mono-substituted by alkoxycarbonyl having a total of from 2 to 5 carbon atoms, by amidocarbonyl or by substituted amidocarbonyl, the amino group of which is mono- or disubstituted by methyl or ethyl or is part of a piperidine, piperazine or morpholine nucleus; alkenyl having from 3 to 5 carbon atoms, alkynyl having from 3 to 5 carbon atoms; alkanoyl having from 1 to 4 carbon atoms; nicotinoyl; benzoyl which is mono-, di- or tri-substituted by alkoxy having 1 or 2 carbon atoms, or mono- or disubstituted by nitro or amino; amidosulfonyl; N-(mono- or di-)alkyl-substituted amidosulphonyl having a total of from 2 to 4 carbon atoms; a radical of formula III

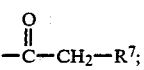

a radical of formula IV

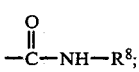

or a radical of formula V

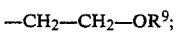

$R^3$ is hydrogen (—H), alkyl having from 1 to 4 carbon atoms, alkoxycarbonylmethyl having a total of from 3 to 6 carbon atoms, amidocarbonylmethyl, N-(mono- or di-)substituted amidocarbonylmethyl having a total of from 2 to 5 carbon atoms, or a radical of formula VII

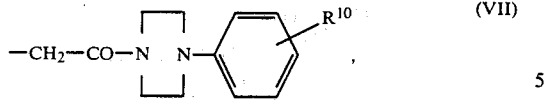

any substituent of N-substituted amidocarbonylmethyl being one of those indicated for N-substituted amidocarbonyl;

$R^4$ is hydrogen (—H), alkyl having from 1 to 4 carbon atoms or phenalkyl which has 1 or 2 carbon atoms in the alkyl radical and is unsubstituted or nuclearly mono- or di-substituted by chlorine;

$R^5$ is hydrogen (—H) or alkoxy having from 1 to 4 carbon atoms;

$R^6$ is hydrogen (—H), or phenyl;

$R^7$ is —$NH_2$, piperidin-1-yl, piperazin-1-yl, 4-(lower alkyl)-piperazin-1-yl or morpholino;

$R^8$ is hydrogen (—H), phenyl or chloro-substituted phenyl;

$R^9$ is hydrogen (—H), phenoxyacetyl or a radical of formula

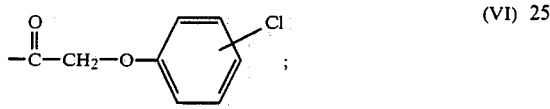

$R^{10}$ is hydrogen (—H) or alkoxy having 1 or 2 carbon atoms; or a physiologically-acceptable acid-addition salt thereof.

7. A compound according to claim 6 wherein
$R^1$ is 2-thienyl;
$R^2$ is alkyl having from 1 to 4 carbon atoms;
$R^3$ is hydrogen (—H) or alkyl having from 1 to 4 carbon atoms.

8. A compound according to claim 28 wherein $R^2$ is alkenyl having from 3 to 5 carbon atoms or alkynyl having from 3 to 5 carbon atoms.

9. A nootropic composition comprising
(a) an effective amount of a physiologically-acceptable compound of formula I

wherein
$R^1$ is phenyl; mono-, di- or tri-substituted phenyl, 2-thienyl, 3-pyridyl or a radical of formula II

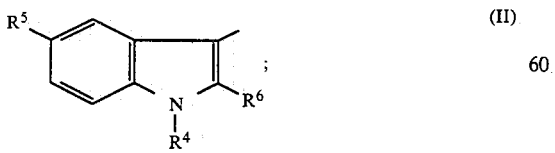

any substituent of substituted phenyl being independently selected from the group consisting of alkoxy having from 1 to 4 carbon atoms, fluoro, alkoxyalkyl having a total of from 2 to 6 carbon atoms or dialkylaminoalkoxy having a total of from 4 to 8 carbon atoms;

$R^2$ is hydrogen (—H); alkyl which has from 1 to 4 carbon atoms and is mono-substituted by alkoxycarbonyl having a total of from 2 to 5 carbon atoms, by amidocarbonyl or by substituted amidocarbonyl, the amino group of which is mono- or disubstituted by methyl or ethyl or is part of a piperidine, piperazine or morpholine nucleus; alkenyl having from 3 to 5 carbon atoms; alkynyl having from 3 to 5 carbon atoms; alkanoyl having from 1 to 4 carbon atoms; nicotinoyl; benzoyl; benzoyl which is mono-, di- or tri-substituted by alkoxy having 1 or 2 carbon atoms, or mono- or di-substituted by nitro or amino; amidosulfonyl, N-(mono- or di-) alkylsubstituted amidosulfonyl having a total of from 2 to 4 carbon atoms; a radical of formula III

a radical of formula IV

or a radical of formula V

$R^3$ is hydrogen (—H), alkyl having from 1 to 4 carbon atoms, alkoxycarbonylmethyl having a total of from 3 to 6 carbon atoms, amidocarbonylmethyl, N-(mono- or di-) substituted amidocarbonylmethyl having a total of from 2 to 5 carbon atoms, or a radical of formula VII

any substituent of N-substituted amidocarbonylmethyl being one of those indicated for N-substituted amidocarbonylmethyl;

$R^3$ being other than hydrogen (—H) when $R^2$ is hydrogen or when $R^1$ is unsubstituted phenyl, $R^4$ is hydrogen (—H), alkyl having from 1 to 4 carbon atoms or phenalkyl which has 1 to 2 carbon atoms in the alkyl radical and is unsubstituted or nuclearly mono- or di-substituted by chlorine;

$R^5$ is hydrogen (—H) or alkoxy having from 1 to 4 carbon atoms;

$R^6$ is hydrogen (—H), or phenyl;

$R^7$ is —$NH_2$, piperidin-1-yl, piperazin-1-yl, 4-(lower alkyl)-piperazin-1-yl or morpholino;

$R^8$ is hydrogen (—H), phenyl or chloro-substituted phenyl;

$R^9$ is hydrogen (—H), phenoxyacetyl or a radical of formula VI

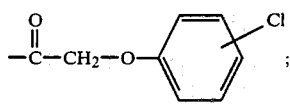

(VI)

$R^{10}$ is hydrogen (—H) or alkoxy having 1 or 2 carbon atoms;

or a physiologically-acceptable acid-addition salt thereof; and (b) a suitable pharmaceutically-acceptable excipient therefor.

10. A composition according to claim 9 wherein $R^1$ is phenyl or mono-, di- or tri-substituted phenyl.

11. A composition according to claim 9 wherein $R^1$ is 2-thienyl.

12. A composition according to claim 9 wherein $R^1$ is 3-pyridyl.

13. A composition according to claim 9 wherein $R^1$ is a radical of formula (II).

14. A composition according to claim 9 in unit-dosage form.

* * * * *